(12) United States Patent
Biermans et al.

(10) Patent No.: US 6,855,846 B2
(45) Date of Patent: Feb. 15, 2005

(54) PROCESS FOR THE PREPARATION OF UREA

(75) Inventors: Andreas Johannes Biermans, Urmond (NL); Kees Jonckers, Roosteren (NL)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 10/415,829

(22) PCT Filed: Nov. 1, 2001

(86) PCT No.: PCT/NL01/00799

§ 371 (c)(1),
(2), (4) Date: Oct. 6, 2003

(87) PCT Pub. No.: WO02/40443

PCT Pub. Date: May 23, 2002

(65) Prior Publication Data

US 2004/0054228 A1 Mar. 18, 2004

(30) Foreign Application Priority Data

Nov. 17, 2000 (NL) ............................................. 1016643

(51) Int. Cl.$^7$ ............................................. C07C 273/04
(52) U.S. Cl. ............................. 564/70; 564/66; 564/67; 564/68; 564/69; 564/71; 564/72
(58) Field of Search .............................. 564/66, 67, 68, 564/69, 70, 71, 72

(56) References Cited

FOREIGN PATENT DOCUMENTS

EP    155 735    10/1998

OTHER PUBLICATIONS

"DSM Carbon Dioxide Stripping Process", *European Chemical News Urea Supplement*, Jan. 17, 1969, pp. 17, 19–20.

*Primary Examiner*—Peter O'Sullivan
(74) *Attorney, Agent, or Firm*—Mayer, Brown, Rowe & Maw LLP

(57) ABSTRACT

Process for the preparation of urea from ammonia and carbon dioxide in which all or part of the liquid ammonia needed for the process is supplied to the high-pressure scrubber in such a way that it is in direct contact with the other streams supplied to this scrubber. In particular in such a way that there is direct contact between the liquid ammonia and the off-gases transferred to the high-pressure scrubber from the urea synthesis reactor. More in particular in such a way that there is direct contact between the liquid ammonia and the off-gases transferred to the high-pressure scrubber from the urea reactor and with the carbamate stream, which is transferred from the low-pressure urea recovery section.

6 Claims, No Drawings

PROCESS FOR THE PREPARATION OF UREA

CROSS REFERENCE TO RELATED APPLICATION

This application is the National Phase of International Application PCT/NL01/00799 filed Nov. 1, 2001 which designated the U.S. and that International Application was published under PCT Article 21(2) in English.

The invention relates to a process for the preparation of urea from ammonia and carbon dioxide.

Urea can be prepared by introducing an ammonia excess together with carbon dioxide into a synthesis zone, which first results in the formation of ammonium carbamate according to the reaction:

$$2NH_3 + CO_2 \rightarrow H_2N-CO-ONH_4$$

Dehydration of the ammonium carbamate formed then results in the formation of urea according to the equilibrium reaction:

$$H_2N-CO-ONH_4 \leftrightarrows H_2N-CO-NH_2 + H_2O$$

The conversion of ammonia and carbon dioxide into urea usually takes place at a pressure of 12–40 MPa and a temperature of 160–250° C. The theoretically attainable conversion of ammonia and carbon dioxide into urea is determined by the thermodynamic position of the equilibrium and depends on for example the $NH_3/CO_2$ ratio, the $H_2O/CO_2$ ratio and the temperature.

In the conversion of ammonia and carbon dioxide to urea, as reaction product a urea synthesis solution is obtained which consists substantially of urea, water, ammonium carbamate and unbound ammonia. In a urea process amongst other things the concentrations of the various components in this reaction product are determined, the measurement results being used to control the process. In particular the molar $NH_3/CO_2$ ratio of the reaction product (N/C ratio) is determined, and this is used to determine the $NH_3$ feed or the $CO_2$ feed to the urea synthesis.

Besides the aforementioned urea synthesis solution, from which urea is recovered in the urea recovery section, in the synthesis zone also a gas mixture of unconverted ammonia and carbon dioxide along with inert gases is formed. Ammonia and carbon dioxide are removed from this gas mixture, which ammonia and carbon dioxide are preferably returned to the synthesis zone. The inert gases are then vented to the atmosphere. The inert gases enter the process via an air supply via for example one of the raw materials, the purpose of this air supply being to improve the corrosion resistance of the equipment.

The synthesis can be carried out in a single reactor or in two reactors. When use is made of two reactors, the first reactor can, for example, be operated using virtually fresh raw materials and the second using raw materials entirely or partly recycled, for example from the urea recovery section.

The conversion of ammonium carbamate into urea and water in the synthesis zone can be accomplished by ensuring a sufficiently long residence time of the reaction mixture in the synthesis zone. The residence time will in general be more than 5 minutes but less than 3 hours.

In practice, various processes are used for the preparation of urea. At first, urea was prepared in so-called conventional urea plants, but since the end of the 1960s urea has mostly been prepared using processes carried out in so-called urea stripping plants.

A conventional urea plant is understood to be a urea plant in which the decomposition of the ammonium carbamate not converted into urea and the expulsion of the usual ammonia excess take place at a substantially lower pressure than the pressure in the synthesis reactor itself. In a conventional urea plant the synthesis reactor is usually operated at a temperature of 180–250° C. and a pressure of 15–40 MPa. In a conventional urea plant, following expansion, dissociation and condensation, the reagents not converted into urea can be returned to the urea synthesis as an ammonium carbamate containing stream. Further, in a conventional urea plant, ammonia and carbon dioxide are fed directly to the urea reactor. The N/C ratio in the urea synthesis in a conventional high-pressure urea process is between 3 and 5.

Initially, such conventional urea plants were designed as so-called 'Once-Through' processes. In these, non-converted ammonia was neutralized with acid (for example nitric acid) and converted into ammonium salts (for example ammonium nitrate). It did not take long until these conventional Once-Through urea processes were replaced with the so-called Conventional Recycle Processes, in which non-converted ammonia and carbon dioxide are recycled to the urea reactor.

A urea stripping plant is understood to be a urea plant in which the decomposition of the ammonium carbamate that is not converted into urea and the expulsion of the customary ammonia excess largely take place in a stripper installed downstream of the synthesis reactor at a pressure that is essentially virtually equal to the pressure in the synthesis reactor. This decomposition/expulsion takes place with heat being supplied and with or without addition of a stripping gas. In a stripping process, carbon dioxide and/or ammonia may be used as stripping gas before these components are added to the reactor. It is also possible to use thermal stripping here. Thermal stripping means that ammonium carbamate is decomposed and the ammonia and carbon dioxide present are removed from the urea solution exclusively by means of the supply of heat. Stripping may also be effected in two or more steps. A process is known, for example, in which a first, purely thermal stripping step is followed by a $CO_2$ stripping step with further addition of heat. The ammonia and carbon dioxide containing gas stream exiting from the stripper is optionally returned to the synthesis reactor via a high-pressure carbamate condenser.

In a recovery section, non-converted ammonia and carbon dioxide are removed from the urea synthesis solution obtained after the stripper, in which process a solution of urea in water is formed. Next, the urea in water solution is converted into urea in the evaporation section by evaporating water at reduced pressure. The non-converted ammonia and carbon dioxide are returned from this recovery section to the synthesis zone as an ammonium carbamate containing stream.

In a urea stripping plant the synthesis reactor is operated at a temperature of 160–240° C. and preferably at a temperature of 170–220° C. The pressure in the synthesis reactor is 12–21 MPa, preferably 12.5–19.5 MPa. The N/C ratio in the synthesis in a stripping plant lies between 2.5 and 5.

A frequently used embodiment for the preparation of urea according to a stripping process is the Stamicarbon $CO_2$ stripping process as described in European Chemical News, Urea Supplement, of 17, Jan. 1969, pages 17–20. The greater part of the gas mixture obtained in the stripping operation is condensed and absorbed, together with the ammonia required for the process, in a high-pressure carbamate condenser, after which the resulting ammonium carbamate is returned to the synthesis zone for the formation of urea. The gas mixture formed in the urea reactor can be sent to a high-pressure scrubber to be absorbed into a low-pressure ammonium carbamate solution that has formed in the urea recovery section. The solution obtained in the high-pressure scrubber is transferred to the synthesis zone, optionally via the high-pressure carbamate condenser.

The high-pressure carbamate condenser may be designed as, for example, a so-called submerged condenser as described in NL-A-8400839. The submerged condenser can be placed in horizontal or vertical position. It is, however, particularly advantageous to carry out the condensation in a horizontal submerged condenser. Such a condenser is also called a pool condenser and is for example described in Nitrogen No. 222, July–August 1996, pp. 29–31. In comparison with other designs of this condenser, the liquid usually has a longer residence time in the pool condenser. This results in the formation of extra urea, which raises the boiling point, so that the difference in temperature between the urea containing ammonium carbamate solution and the cooling medium increases, resulting in better heat transfer.

The functions of reactor, pool condenser and high-pressure scrubber can be combined into one or two high-pressure vessels, the functionality of these process steps being separated by means of partitions, designed for small pressure differences, in these high-pressure vessels. A special advantage of this is that considerable savings in investments can be realized since the amount of high-pressure piping that needs to be installed is much lower. In addition, this enhances the plant's reliability since the number of high-pressure joints between piping and equipment that are susceptible to leaks is much reduced. Examples of these embodiments are:

pool condenser combined with a horizontal reactor as reported in U.S. Pat. No. 5,767,313, in which the pool reactor is described.
high-pressure scrubber integrated into pool condenser.
high-pressure scrubber integrated into reactor.
high-pressure scrubber and pool condenser combined in a single apparatus.

After the stripping treatment the stripped urea synthesis solution is expanded to a low pressure and evaporated in the urea recovery section, following which urea is released and a low-pressure ammonium carbamate stream is recirculated to the synthesis section. Depending on the process, this ammonium carbamate may be recovered in either a single step or in a plurality of process steps operating at different pressures.

In the preparation of urea from $NH_3$ and $CO_2$ in a Stamicarbon $CO_2$ stripping plant ammonia and carbon dioxide are initially condensed in the high-pressure carbamate condenser, so that ammonium carbamate is formed. From this carbamate condenser a gas and liquid stream is then directed to the reactor in which part of the ammonium carbamate is converted into urea and water. The off-gas leaving the reactor is subsequently scrubbed in a high-pressure scrubber with an ammonium carbamate solution that has formed in the recovery section. The remaining off-gas is then expanded and, at lower pressures, freed of all $NH_3$ and vented. This results in another stream containing small amounts of $NH_3$ and $CO_2$, which is returned to the urea synthesis.

In the high-pressure scrubber in the synthesis section of a urea plant operating according to the $CO_2$ stripping principle, the following two situations can be distinguished:

1: Almost all ammonia and carbon dioxide are scrubbed out of the reactor off-gas by means of cooling with the aid of a heat exchanger and subsequent scrubbing with the low-pressure ammonium carbamate solution formed in the recovery section that is to be supplied to the synthesis. In that cases the inerts content after scrubbing is higher than 50 vol. %. This situation is described in the article in European Chemical News referenced above.
2: Part of the ammonia and carbon dioxide are scrubbed out of the reactor off-gas, scrubbing being effected only with the low-pressure ammonium carbamate solution formed in the recovery section that is to be supplied to the synthesis. The inerts content after scrubbing is lower than 50 vol. %, in particular lower than 30 vol. %. As a rule the inerts content after scrubbing is higher than 10 vol. %. An example of this is the process described in U.S. Pat. No. 5,767,313, in which the inerts content after scrubbing amounts to approximately 20–24 vol. %. The reactor off-gas initially contains between 6 and 8 vol. % inerts in both situation 1 and situation 2.

In the Stamicarbon $CO_2$ stripping process the carbon dioxide, as described above, is supplied to the synthesis via the stripper, while the ammonia is supplied to the high-pressure carbamate condenser as described in European Chemical News, Urea supplement of 17 Jan. 1969, pp. 17–20, or to the condenser part of the pool reactor as described in U.S. Pat. No. 5,7676,313.

It has been found that the liquid ammonia needed for the process can advantageously be supplied fully or partly to the high-pressure scrubber in such a way that it is in direct contact with the other streams supplied to this scrubber. The other streams supplied to the high-pressure scrubber consist substantially of the synthesis reactor off-gases and the low-pressure carbamate stream formed in the recovery section. In particular, in the high-pressure scrubber direct contact is made between the liquid ammonia and the off-gases transferred from the urea reactor to the high-pressure scrubber. More in particular, in the high-pressure scrubber direct contact is made between the liquid ammonia and the off-gases transferred from the urea reactor to the high-pressure scrubber and with the carbamate stream transferred from the low-pressure urea recovery section. The amount of ammonia supplied to the high-pressure scrubber is at least 40 wt. % of the total amount of $NH_3$ needed for the process. Preferably, however, all the ammonia needed for the process is supplied via the high-pressure scrubber before being passed to the urea synthesis. If not all ammonia is supplied via the high-pressure scrubber, then the remainder of the ammonia needed for the process is preferably passed to the urea synthesis reactor via the high-pressure carbamate condenser, optionally via an ejector.

It has been found that scrubbing of the reactor off-gas with the $NH_3$ supplied resulted in scrubber off-gas containing virtually no $CO_2$. Due to the low $CO_2$ content of the off-gas, only a small amount of water is needed for the $CO_2$ transport in the recycle stream that returns the $NH_3$ and $CO_2$ that have not been converted into urea back to the synthesis. As a consequence, less $H_2O$ is returned to the reactor, so that a more favourable position of the reaction equilibrium is achieved.

It has also been found that when the cold $NH_3$ to be supplied to the synthesis was supplied directly to the scrubber, more reactor off-gas was drawn in by the scrubber, as a result of which the overall inerts content of the reactor off-gas decreased. At the same reactor pressure this led to an increase in the partial system pressure, so that the corresponding system temperature and thus also the reaction rate and the degree of conversion increased.

In addition, it has been found that the temperature in the high-pressure carbamate condenser was higher. The higher temperature in the high-pressure carbamate condenser caused the pressure, and thus the temperature, of the low-pressure steam produced to increase. The energy thus stored can be put to good use elsewhere.

Another major advantage is that in case of virtually complete scrubbing, which is achieved by directing the $NH_3$ needed for the process to the high-pressure scrubber, no heat-exchanging surface area is needed in the scrubber, which implies that the entire conditioned cooling water system with pumps, start-up jacketing and cooling water cooler is no longer necessary, which yields a large advantage in terms of investment. It also implies a reduction in maintenance costs.

In the literature various processes are described in which all the required liquid ammonia is passed through the high-pressure scrubber via a heat-exchanging area before being sent to the condenser part. This does not involve any direct contact with the reactor off-gas, so that the above-mentioned advantages are partly lost. An example in which this process is applied is described inter alia in EP-A-834 501.

The process described by the invention is eminently suited for improvement and optimization of existing urea plants in which a high-pressure scrubber is present and in which the carbamate stream from the low-pressure part is directed to the high-pressure scrubber and the resulting carbamate stream from the high-pressure scrubber is transferred to the synthesis zone, optionally via a high-pressure carbamate condenser.

The invention is further elucidated below on the basis of the following examples.

EXAMPLE I AND COMPARATIVE EXAMPLES A AND B (VIRTUALLY COMPLETE SCRUBBING)

The examples were carried out for a 2000 t/day urea plant operating according to the standard Stamicarbon $CO_2$ stripping process as described in European Chemical News, Urea Supplement, of 17, Jan. 1969, pages 17–20.

In comparative example A all $NH_3$ is fed to the carbamate condenser via an ejector, which as a rule is customary in the Stamicarbon $CO_2$ process. The carbamate stream from the high-pressure scrubber is transferred to the synthesis zone via the high-pressure carbamate condenser via an ejector driven by the ammonia required for the process.

Comparative example B is carried out, with all $NH_3$ needed for the Stamicarbon $CO_2$ stripping process being passed to the condenser part via a heat-exchanging surface through the high-pressure scrubber.

In example I the total amount of $NH_3$ to be supplied to the process is supplied to the high-pressure scrubber in such a way that there is direct contact in the high-pressure scrubber between the liquid ammonia and the off-gases transferred from the urea reactor to the high-pressure scrubber and with the low-pressure carbamate stream from the urea recovery section.

Results of example I and comparative examples A and B for situation 1 (virtually complete scrubbing) in a standard Stamicarbon stripping process are presented in table 1:

TABLE 1

|  | $CO_2$ in scrubber off-gas (kg/hr) | Pressure of l.p. steam (kg/cm$^2$) | Inerts in R.G. (Vol. %) | Inerts after scrubber (Vol. %) | Scrubber heat discharge (MW) |
|---|---|---|---|---|---|
| Example A | 124 | 4.5 | 7 | 89 | 4.0 |
| Example B | 124 | 4.5 | 7 | 89 | 4.0 |
| Example I | 21 | 4.5 | 7 | 83 | 0.0 |

NB:
l.p. = low pressure
R.G. = reactor gas

EXPERIMENT II AND COMPARATIVE EXAMPLES C AND D

These experiments started from situation 2: partial scrubbing and use of a pool reactor as described in U.S. Pat. No. 5,767,313 and Nitrogen July/August 1996, pp. 29–31.

In comparative example C all $NH_3$ was supplied directly to the condenser part of the pool reactor as described in U.S. Pat. No. 5,767,313. Comparative example D is carried out with all of the ammonia needed for the process being passed through the high-pressure scrubber via a heat-exchanging area before being directed to the condenser part of the pool reactor.

In the experiments for situation 2 in all cases the inerts content after scrubbing was set at about 22 vol. %. In example II the total amount of $NH_3$ to be supplied to the process is supplied to the high-pressure scrubber in such a way that there is direct contact in the high-pressure scrubber between the liquid ammonia and the off-gases transferred to the high-pressure scrubber from the urea reactor and with the low-pressure carbamate stream from the recovery section.

Results of example II in situation 2 (partial scrubbing) as well as the comparative examples C and D are presented in table 2.

TABLE 2

|  | $CO_2$ in off-gas (kg/hour) | Pressure of l.p. steam (kg/cm$^2$) | Inerts in R.G. (Vol. %) |
|---|---|---|---|
| Example C | 670 | 4.4 | 8.2 |
| Example D | 393 | 4.64 | 4.4 |
| Example II | 27 | 4.51 | 4.4 |

What is claimed is:

1. Process for the preparation of urea from ammonia and carbon dioxide, characterized in that all or part of the liquid ammonia needed for the process is supplied to the high-pressure scrubber in such a way that it is in direct contact with the other streams supplied to this scrubber.

2. Process according to claim 1, characterized in that there is direct contact between the liquid ammonia and the off-gases transferred to the high-pressure scrubber from the urea reactor.

3. Process according to claim 1, characterized in that there is direct contact between the liquid ammonia and the off-gases transferred to the high-pressure scrubber from the urea reactor and with the carbamate stream transferred from the low-pressure urea recovery section.

4. Process according to claim 1, characterized in that the amount of ammonia supplied to the high-pressure scrubber is at least 40 wt. % of the total amount of $NH_3$ needed for the process.

5. Process according to claim 1, characterized in that all liquid ammonia needed for the process is supplied via the high-pressure scrubber before being transferred to the urea synthesis.

6. Process according to claim 4, characterized in that the remainder of the ammonia needed for the process is passed to the urea synthesis reactor via the high-pressure carbamate condenser.

* * * * *